(12) United States Patent
Kim

(10) Patent No.: US 10,390,638 B2
(45) Date of Patent: Aug. 27, 2019

(54) SMART PILLOW SYSTEM AND MANUFACTURING METHOD THEREFOR

(71) Applicant: GIOCLAVIS CO. LTD., Suwon-si, Gyeonggi-do (KR)

(72) Inventor: Jin Young Kim, Suwon-si (KR)

(73) Assignee: GIOCLAVIS CO. LTD., Suwon-si (KR)

( * ) Notice: Subject to any disclaimer, the term of this patent is extended or adjusted under 35 U.S.C. 154(b) by 424 days.

(21) Appl. No.: 15/125,013

(22) PCT Filed: Mar. 18, 2015

(86) PCT No.: PCT/KR2015/002641
§ 371 (c)(1),
(2) Date: Sep. 9, 2016

(87) PCT Pub. No.: WO2015/190674
PCT Pub. Date: Dec. 17, 2015

(65) Prior Publication Data
US 2017/0013979 A1    Jan. 19, 2017

(30) Foreign Application Priority Data

Jun. 10, 2014  (KR) .................. 10-2014-0069923
Jan. 19, 2015  (KR) .................. 10-2015-0008608

(51) Int. Cl.
*A47G 9/10*     (2006.01)
*A61M 21/02*  (2006.01)
(Continued)

(52) U.S. Cl.
CPC .............. *A47G 9/1045* (2013.01); *A61F 5/56* (2013.01); *A61M 21/02* (2013.01);
(Continued)

(58) Field of Classification Search
CPC ............. A47G 9/10; A47G 9/1045; A47G 2009/1018; A47G 2009/006; A61F 5/56;
(Continued)

(56) References Cited

U.S. PATENT DOCUMENTS 3,290,450 A * 12/1966 Majoros ................. H04R 5/023
381/182
3,621,155 A * 11/1971 Pruitt ................... A47G 9/1045
381/182
(Continued)

FOREIGN PATENT DOCUMENTS

JP          61-5090 U      1/1986
JP          3-69466 U      7/1991
(Continued)

OTHER PUBLICATIONS

Japanese Office Action dated Mar. 14, 2017, issued by the Japanese Patent Office in corresponding application JP 2016-527960.
(Continued)

*Primary Examiner* — Robert G Santos
*Assistant Examiner* — David R Hare
(74) *Attorney, Agent, or Firm* — Stein IP, LLC

(57) ABSTRACT

The present invention relates to a smart pillow system and a manufacturing method therefor. The smart pillow system detects brain wave information of a sleeper who sleeps on a pillow, notifies a smart phone of the brain wave information, receives the most suitable music or acoustic sound for the sleeper's sound sleep from the smart phone on the basis of the sleeper's brain wave information, and provides the received music or acoustic sound to the sleeper through the pillow. The smart pillow system, according to the present invention, comprises a pillow in which a speaker-shaped recess and a wire-shaped groove are formed at locations where a speaker and an electric wire are to be inserted into
(Continued)

a single air mesh by cutting away the air mesh, the speaker is attached to the speaker-shaped recess through an adhesive, the electric wire is inserted into the wire-shaped groove and is fixed to the wire-shaped groove while being tied with a cable tie, an adhesive is applied along the wire-shaped groove into which the electric wire is inserted, a membrane that has the shape of a mesh is attached to the speaker to waterproof the speaker, a communication unit is connected to the electric wire to transmit/receive a signal to/from a user terminal, and after other air meshes are stacked on the top and bottom of the single air mesh, the single air mesh and the other air meshes are covered with a cover that has the shape of a pillow.

6 Claims, 16 Drawing Sheets

(51) Int. Cl.
*A61F 5/56* (2006.01)
*A47G 9/00* (2006.01)
*A61M 21/00* (2006.01)

(52) U.S. Cl.
CPC ............ *A47G 2009/006* (2013.01); *A61M 2021/0027* (2013.01); *A61M 2205/52* (2013.01); *A61M 2207/00* (2013.01); *A61M 2230/10* (2013.01)

(58) Field of Classification Search
CPC .......... A61M 2207/10; A61M 2205/52; A61M 21/00; A61M 21/02; A61M 2021/0027; A61M 2230/10
See application file for complete search history.

(56) References Cited

U.S. PATENT DOCUMENTS

| | | | | |
|---|---|---|---|---|
| 4,038,499 A * | 7/1977 | Yeaple | ............... | H04R 5/023 381/301 |
| 4,782,533 A * | 11/1988 | Haynie | ............... | A47G 9/1045 381/301 |
| 4,862,438 A * | 8/1989 | Fry | ............... | A47C 7/72 369/19 |
| 5,123,133 A * | 6/1992 | Albert | ............... | A47G 9/10 381/301 |
| 5,313,678 A * | 5/1994 | Redewill | ............... | A47C 21/003 297/393 |
| 6,098,220 A * | 8/2000 | Momma | ............... | A47G 9/1009 5/636 |
| 6,236,621 B1 * | 5/2001 | Schettino | ............... | A47G 9/1045 368/10 |
| 7,248,915 B2 * | 7/2007 | Ronnholm | ............... | A61M 21/00 340/575 |
| 7,685,661 B2 * | 3/2010 | Popilek | ............... | A47G 9/1045 381/301 |
| 8,566,986 B1 * | 10/2013 | Chu | ............... | A47G 9/1045 5/636 |
| 9,003,582 B2 * | 4/2015 | Armbruster | ............... | A61M 21/02 5/639 |
| 10,022,003 B1 * | 7/2018 | Edoria | ............... | G04G 13/021 |
| 10,063,952 B2 * | 8/2018 | Fuchs | ............... | H04R 5/023 |
| 10,201,236 B1 * | 2/2019 | Cloud | ............... | A47D 13/08 |
| 2006/0293608 A1 * | 12/2006 | Rothman | ............... | A61B 5/0476 600/545 |
| 2007/0124862 A1 * | 6/2007 | Beyda | ............... | A47G 9/1045 5/639 |
| 2008/0091862 A1 * | 4/2008 | Hiraka | ............... | H04B 10/278 710/110 |
| 2008/0201855 A1 * | 8/2008 | Groves | ............... | A47D 5/006 5/655 |
| 2009/0089931 A1 * | 4/2009 | Vandenbelt | ............... | A47G 9/1045 5/639 |
| 2010/0097197 A1 * | 4/2010 | Sowada | ............... | H04B 10/1149 340/286.07 |
| 2010/0145167 A1 * | 6/2010 | Im | ............... | A47G 9/1045 600/301 |
| 2012/0029322 A1 * | 2/2012 | Wartena | ............... | A61B 5/0476 600/301 |
| 2012/0142999 A1 * | 6/2012 | Albu | ............... | A47G 9/0215 600/26 |
| 2013/0035541 A1 * | 2/2013 | Kashima | ............... | A61M 21/02 600/26 |
| 2014/0366273 A1 * | 12/2014 | Davis, II | ............... | G04G 13/02 5/639 |

FOREIGN PATENT DOCUMENTS

| | | |
|---|---|---|
| JP | H 4-27868 B2 | 5/1992 |
| JP | 2002-125825 A | 5/2002 |
| JP | 2006-129235 A | 5/2006 |
| JP | 2007-175388 A | 7/2007 |
| JP | 2011-255008 A | 12/2011 |
| JP | 2013-31542 A | 2/2013 |
| KR | 10-2006-0034476 A | 4/2006 |
| KR | 10-2007-0038960 A | 4/2007 |
| KR | 10-2010-0128032 A | 12/2010 |
| KR | 10-2013-0079774 A | 7/2013 |
| KR | 10-2014-0057844 A | 5/2014 |

OTHER PUBLICATIONS

International Search Report dated Jul. 20, 2015, issued to International Application No. PCT/KR2015/002641.
Korean Office Action dated Jan. 21, 2016, issued to Korean Application No. 2016-527960.
Japanese Office Action dated Jul. 29, 2016, issued to Japanese Application No. 2016-527960.

* cited by examiner

SMART PILLOW SYSTEM AND MANUFACTURING METHOD THEREFOR

CROSS-REFERENCE TO RELATED APPLICATIONS

This application is a national stage of International Application No. PCT/KR2015/002641, filed Mar. 18, 2015, which claims the benefit of priority to Korean Application No. 10-2014-0069923, filed Jun. 10, 2014, and Korean Application No. 10-2015-0008608, filed Jan. 19, 2015, in the Korean Intellectual Property Office, the disclosures of which are incorporated in their entireties herein by reference.

TECHNICAL FIELD

Exemplary embodiments of the present invention relate to a smart pillow system and a method for manufacturing the same capable of notifying a user's smart phone managing a sleeper of a case in which the sleeper wakes up while a sound sleep state of the sleeper who is sleeping on the pillow is sensed and providing music or sound most suitable to enable the sleeper to get a sound sleep based on brainwave information of the sleeper to the sleeper through the pillow, to thereby enable the sleeper to get a sound sleep again.

BACKGROUND ART

Generally, a sound sleep in a relaxed state affects human health, and therefore a proper use of a pillow for sleep and a function thereof regulates body's metabolism and affects a human body.

The reason why a sleeper feels comfortable only when he/she sleeps on a pillow with a certain height for a sound sleep is that a cervical vertebra supporting a head is not located on the same straight line as a spine but is formed to have a certain curved line, and therefore when a sleeper sleeps on a pillow with a height approximating a deviation in height between the cervical vertebra and the spine of the human body, the sleeper may be seated on the pillow without being sagged thanks to the pillow.

When the height of the pillow is high or low, the cervical vertebra is instantly hardened in a state in which it is spread straight or excessively bowed. In this case, the problem that nerves or muscles around the cervical vertebra are stimulated while the cervical vertebra returns to its shape when he/she stands up and thus a user feels heavy, and in severe cases, the spine is twisted may occur.

As a result, a functional pillow protecting the cervical vertebra has been used in recent. The functional pillow is configured to include a main body made of at least any one of materials such as memory foam, sponge, cotton, and latex and having a flat bottom surface, a cervical vertebra support formed to protrude at a middle part of an upper surface of the main body and supporting a neck to bend a user's head back, an occipital support extended to a back of the cervical vertebra support to be integrally formed with the cervical vertebra support and supporting a user's head occipital region, a shoulder support extended to a front of the occipital support to be integrally formed with the occipital support and downwardly inclined to support a user's shoulder region, and an air-permeable cover enclosing and supporting an outside of the main body and applying any one of anion, a far infrared ray radiating material, and an aromatic to an inside thereof in a powder or phlegmatic temperament form.

There is a problem in that the pillow is manufactured by compression-molding expensive materials such as urethane and latex, and therefore is very difficult to manufacture, an upper end part of the pillow is provided with a bone conduction speaker, and therefore a headache phenomenon occurs when the pillow is used for a long time, and a user's head deviates from the pillow when the head moves left and right, and therefore the user does not get a pleasant sound sleep.

DISCLOSURE

Technical Problem

An object of the present invention relates to a smart pillow system and a method for manufacturing the same capable of notifying a user's smart phone managing a sleeper of a case in which the sleeper wakes up while a sound sleep state of the sleeper who is sleeping on the pillow is sensed and providing music or sound most suitable to enable the sleeper to get a sound sleep based on brainwave information of the sleeper to the sleeper through the pillow, to thereby enable the sleeper to get a sound sleep again.

Technical Solution

In accordance with one aspect of the present invention, there is provided a smart pillow system including a pillow, wherein one air mesh is provided with a speaker-shaped groove and a line-shaped groove by cutting each of the locations at which a speaker and a wire are inserted, the speaker is attached to the speaker-shaped groove by an adhesive, the wire is inserted into the line-shaped groove and is tied by a cable tie to be fixed, the adhesive is applied along the line-shaped groove into which the wire is inserted, the speaker is attached with a mesh-shaped membrane for waterproofing, a communication unit for transmitting and receiving a signal to and from a user terminal is connected to the wire, other air meshes are laminated above and under the one air mesh, and the other air meshes including the one air mesh are covered with a pillow-shaped outer cover.

The pillow may generate an alarm signal when sensing that the sleeper wakes up from a sleeping state and may be thus in a non-sleeping state, measure the brainwave wave of the sleeper and transmit the measured brainwave information of the sleeper to the user terminal through the communication unit along with the alarm signal, and receives a sound sleep control signal based on the brainwave information of the sleeper from the user terminal to output the music or the sound to enable the sleeper get a sound sleep, and the user terminal may receive from the pillow the brainwave information of the sleeper along with the alarm signal notifying that the sleeper wakes up from the sleeping state and transmit the sound sleep control signal including the music or the sound suitable to enable the sleeper to keep the sound sleep based on the brainwave information of the sleeper to the pillow.

When more than one pillow is present around the user terminal, the user terminal may be operated as a first master terminal and a first pillow at a shortest distance from the user terminal may be operated as a first slave terminal to transmit the sound sleep control signal from the user terminal that is the first master terminal to the first pillow that is the first slave terminal and the first pillow may be operated as a second master terminal when a second pillow is present at the shortest distance therefrom and the second pillow may be operated as a second slave terminal to transmit the sound sleep control signal from the first pillow that is the second master terminal to the second pillow that is the second slave terminal, and thus the pillows adjacent to each other at a short distance may be as the master terminal and the slave terminal to operate an N−1-th pillow as an N-th master terminal when an N-th pillow is present at the shortest distance therefrom and operate the N-th pillow as an N-th slave terminal to thereby transmit the sound sleep control signal from the N−1-th pillow that is the N-th master terminal to the N-th pillow that is the N-th slave terminal, such that as the sound sleep control signal is sequentially transmitted through a linear network from the first pillow to the N-th pillow, the first pillow to the N-th pillow are operated based on the sound sleep control signal.

When time taken to transmit the sound sleep control signal from the master terminal to the slave terminal is A seconds, time taken to transmit the sound sleep control signal from the user terminal to the N-th pillow through the first pillow may be calculated as A seconds*N.

The pillow may communicate with the user terminal through the communication unit in a wired or wireless manner and the pillow may include: a main body frame configured to support a head of the sleeper; a sleep sensing unit configured a sleeping state and a non-sleeping state using a sensing sensor included in the main body frame; a brainwave measurement unit configured to measure the brainwave of the sleeper and transmit the measured brainwave information to the user terminal; a non-sleep alarm unit configured to output an alarm signal notifying that the sleeper wakes up from the sleeping state when the non-sleeping state of the sleeper is sensed by the sleep sensing unit; and a sound output unit configured to output the music or the sound enabling the sleeper get the sound sleep based on a sound sleep control signal received from the user terminal.

The user terminal includes: a memory unit configured to store environment information including the music or the sound corresponding to the brainwave information; an input unit configured to select the music or the sound corresponding to the brainwave information; an alarm processing unit configured to output the alarm signal received from the pillow on a screen or output the alarm signal as a sound; and an application unit configured to transmit the sound sleep control signal, that enables the sleeper to get the sound sleep based on the brainwave information of the sleeper, to the pillow.

The main body frame may have a central part provided with a through hole so that a head of the sleeper is seated and have a pillow shape in which an air mesh having a concave shape inclined from an outside to the through hole is laminated sheet by sheet, and have a concave shape inclined from the outside to the through hole.

The brainwave measurement unit may detect a current on a scalp using a sensing sensor configured of an electrode to measure an electrical signal of a brain including a delta wave, a theta wave, an alpha wave, a beta wave, and a gamma wave.

In accordance with another aspect of the present invention, a method for manufacturing a smart pillow includes: (a) forming a speaker-shaped groove and a line-shaped groove at one air mesh by cutting a location at which speakers A1 and B1 and a wire C are inserted; (b) inserting the wire into the line-shaped groove and attaching the speaker to the speaker-shaped groove by an adhesive; (c) tying the wire inserted into the line-shaped groove with an air-mesh fabric by a cable tie at a predetermined interval and fixing the wire; (d) connecting the wire to a communication unit for transmitting and receiving a signal to and from a user terminal; (e) laminating other air meshes above and under the one air mesh; and (f) covering other laminated air meshes with a pillow-shaped outer cover.

In the step (a), a rectangular shape may be indicated at a location at which the speaker is inserted into the one air-mesh fabric, a line may be indicated along the location at which the wire is inserted, the location at which the speaker and the wire are inserted may be cut to form a speaker-shaped groove and a line-shaped groove.

In the step (a), the location at which the speaker and the wire are inserted may be provided with a speaker-shaped groove and a line-shaped groove by being not completely cut at a depth corresponding to a half of a thickness of the one air mesh but cut only by half.

In the step (b), the speaker may be waterproofed while being attached with a mesh-shaped membrane.

In the step (a) or (b), an interval between a left speaker A1 and a right speaker B1 may be maintained so that a left ear tragus portion a1 and a right ear tragus portion b1 of the sleeper correspond to the speakers A1 and B1 located at the air-mesh fabric.

The interval between the left speaker A1 and the right speaker B1 may be maintained at 1800 mm to 2000 mm.

In the step (c), an adhesive may be applied along the line-shaped groove into which the wire is inserted to additionally fix the wire.

In the step (c), when the air-mesh fabric is applied with the adhesive along the line-shaped groove into which the wire C is inserted, the line-shaped groove and the wire C both may be applied with the adhesive in such a manner that the line-shaped groove is completely filled.

Advantageous Effects

According to the present invention, the pillow is made of the 3D air mesh material to give the cushion sense like the latex material and have the high air-permeability, such that the sleeper may get the sound sleep under a cold state without the pillow being clammy sweat.

Further, the middle and lower end part of the pillow is provided with the sound output speaker, and thus the pillow does not feel hard and the pillow receives sound from the smart phone in the wireless scheme, not in the wired manner, such that the pillow may continuously play the sound even though the sleeper rolls over in his/her sleep.

Further, the music or the sound to enable the sleeper to get the sound sleep best may be selected and provided based on the brainwave information of the sleeper previously stored in the smart phone through the application, such that the sleeper may get the sound sleep again.

DESCRIPTION OF DRAWINGS

The above and other objects, features and advantages of the present invention will become apparent from the following description of preferred embodiments given in conjunction with the accompanying drawings, in which.

BEST MODE

Figure 1:
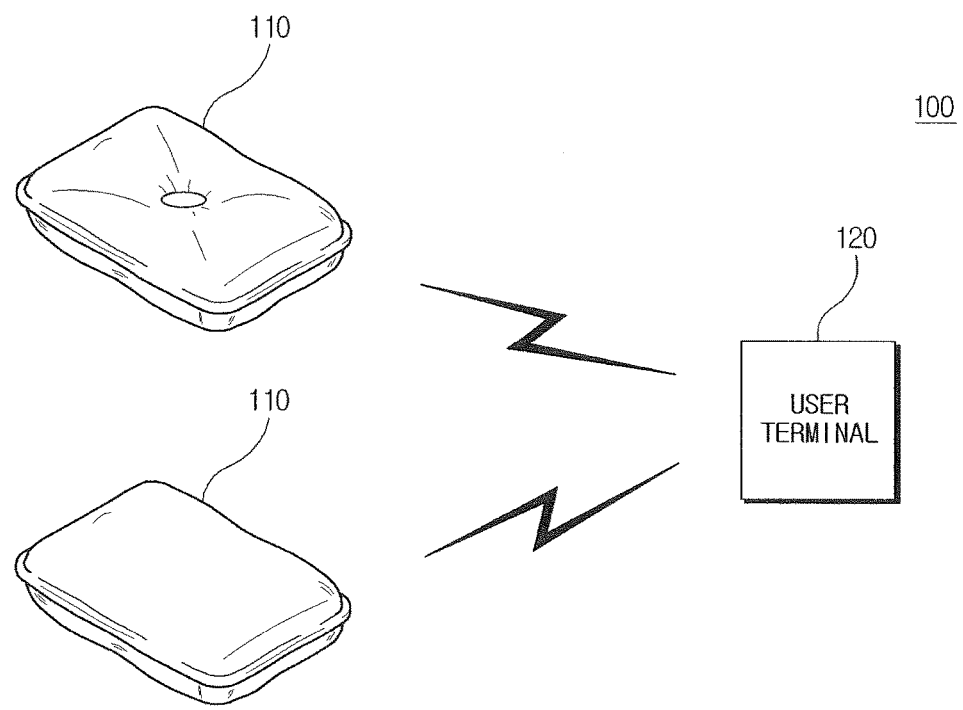
FIG. 1 is a diagram schematically illustrating the whole configuration of a smart pillow system according to an exemplary embodiment of the present invention.

Hereinafter, exemplary embodiments of the present invention will be described in detail with reference to the accompanying drawings so that those skilled in the art may easily practice the present invention. As those skilled in the art would realize, the described embodiments may be modified in various different ways, all without departing from the spirit or scope of the present invention.

A part irrelevant to the description will be omitted to clearly describe the present invention, and the same elements will be designated by the same reference numerals throughout the specification.

In addition, throughout the present specification, when any one part is referred to as being "connected to" another part, it means that any one part and another part are "directly connected to" each other or are "electrically connected to" each other with the other part interposed therebetween. In addition, unless explicitly described to the contrary, "comprising" any components will be understood to imply the inclusion of other elements rather than the exclusion of any other elements.

The mention that any portion is present "over" another portion means that any portion may be directly formed on another portion or a third portion may be interposed between one portion and another portion. In contrast, the mention that any portion is present "just over" another portion means that a third portion may not be interposed between one portion and another portion.

Terms used throughout the specification, 'first', 'second', 'third', etc. can be used to describe various portions, components, regions, layers, and/or sections but are not limited thereto. These terms are used only to differentiate any portion, component, region, layer, or section from other portions, components, regions, layers, or sections. Therefore, a first portion, component, region, layer, or section which will be described below may be mentioned as a second portion, component, region, layer, or section without departing from the scope of the present invention.

Terminologies used herein are to mention only a specific exemplary embodiment, and does not limit the present invention. Singular forms used herein include plural forms as long as phrases do not clearly indicate an opposite meaning. A term "including" used in the present specification concretely indicates specific properties, regions, integer numbers, steps, operations, elements, and/or components, and is not to exclude presence or addition of other properties, regions, integer numbers, steps, operations, elements, components, and/or a group thereof.

The term expressing the relative space of "under", "over", and the like may be used to more easily describe the relationship between other portions of one portion which is illustrated in the drawings. The terms intend to include other meanings or operations of apparatuses which are being used along with the intended meaning in the drawings. For example, overturning the apparatus in the drawings, any portions described as being positioned "under" other portions will be described as being postioned "over" other portions. Therefore, the exemplified term "under" includes both of the up and down directions. An apparatus may rotate by 90° or may rotate at different angles and the term expressing a relative space is interpreted accordingly.

All terms including technical terms and scientific terms used herein have the same meaning as the meaning generally understood by those skilled in the art to which the present invention pertains unless defined otherwise. Terms defined in a generally used dictionary are additionally interpreted as having the meaning matched to the related art document and the currently disclosed contents and are not interpreted as ideal or formal meaning unless defined.

Hereinafter, exemplary embodiments of the present invention so as to be easily practiced by a person skilled in the art to which the present invention pertains will be described in detail with reference to the accompanying drawings. However, the present invention may be modified in various different ways and is not limited to the embodiments provided in the present description.

FIG. 1 is a diagram schematically illustrating the whole configuration of a smart pillow system according to an exemplary embodiment of the present invention.

Referring to FIG. 1, a smart pillow system 100 according to an exemplary embodiment of the present invention includes a pillow 110 and a user terminal 120.

The pillow 110 has a structure in which one air mesh is provided with a speaker-shaped groove and a line-shaped groove by cutting each of the locations at which a speaker and a wire are inserted, the speaker is attached to the speaker-shaped groove by an adhesive, the wire is inserted into the line-shaped groove and is tied by a cable tie to be fixed, the adhesive is applied along the line-shaped groove into which the wire is inserted, the speaker is attached with a mesh-shaped membrane for waterproofing, a communication unit for transmitting and receiving a signal to and from a user terminal is connected to the wire, other air meshes having a predetermined thickness are laminated above and under the one air mesh, are covered with a pillow-shaped outer cover. This will be described in more detail with reference to FIG. 6.

The pillow 110 generates an alarm signal when sensing that the sleeper wakes up from a sleeping state and is thus in a non-sleeping state, measures the brainwave wave of the sleeper and transmits the measured brainwave information of the sleeper to the user terminal 120, and receives a sound sleep control signal based on the brainwave information of the sleeper from the user terminal 120 to output the music or the sound to enable the sleeper get a sound sleep.

Further, the pillow 110 may have a structure in which it has a central part provided with a through hole 212 so that a head of the sleeper may be stably seated and has a concave shape from an outside to the through hole 212 is laminated sheet by sheet, and has a concave shape inclined from the outside to the through hole. That is, a pillow for adult has a structure in which a central part is not provided with a through hole and a pillow for children has a structure in which a central part is provided with a through hole to help a head to be seated on the through hole to thereby form a head shape.

Further, the pillow 110 is made of a 3D air mesh material that has good air permeability and transfers tactile sensation to a user.

Further, the pillow 110 has a structure in which a speaker through which a sound is output is provided at a lower part of the pill 1100 and a sound signal output from the speaker is transferred to an upper part thereof through the 3D air mesh to be provided to a sleeper.

The user terminal 120 receives from the pillow 110 the brainwave information of the sleeper along with an alarm signal notifying that the sleeper wakes up from the sleeping state and transmits the sound sleep control signal including the music or the sound suitable to enable the sleeper to keep the sound sleep based on the brainwave information of the sleeper to the pillow 110.

Here, the sound sleep signal includes a music or sound signal corresponding to a tone most suitable to enable a sleeper to get a sound sleep based on brainwave information of the sleeper and the brainwave information includes a delta wave, a theta wave, an alpha wave, a beta wave, and a gamma wave acquired by detecting a current on a scalp using a sensing sensor configured of an electrode.

Figure 2:
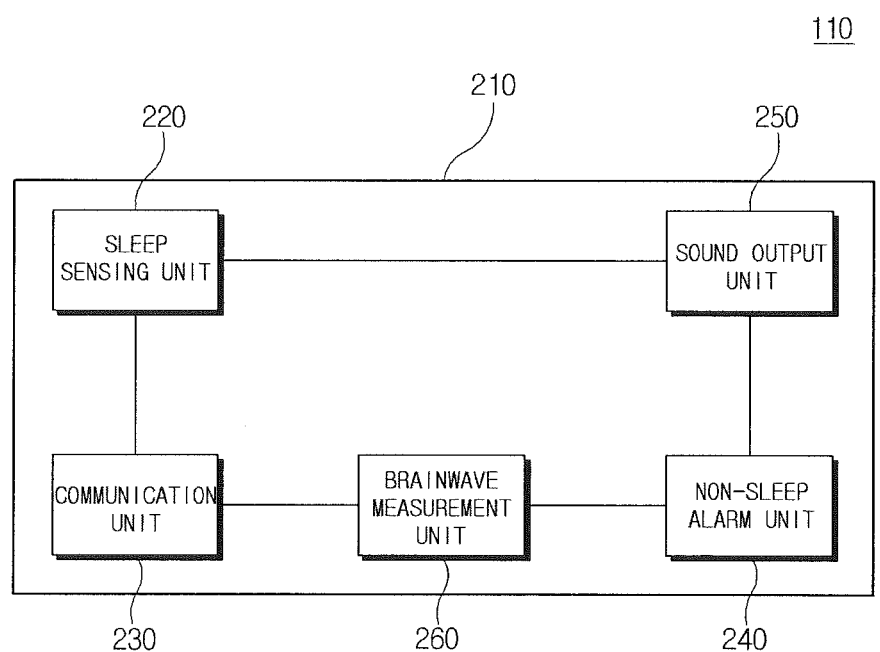
FIG. 2 is a diagram schematically illustrating an internal configuration of the pillow according to the exemplary embodiment of the present invention.

FIG. 2 is a diagram schematically illustrating an internal configuration of the pillow according to the exemplary embodiment of the present invention.

Referring to FIG. 2, the pillow 110 according to the exemplary embodiment of the present invention includes a main body frame 210, a sleep sensing unit 220, a communication unit 230, a non-sleep alarm unit 240, a sound output unit 250, and a brainwave measurement unit 260.

Further, the body frame 210 has a structure in which it has a central part provided with the through hole 212 so that the head of the sleeper may be stably seated and has a concave shape from an outside to the through hole 212. That is, the body frame 210 has a pillow shape in which the central part is provided with the through hole and a thin air mesh is laminated sheet by sheet, and it has a concave shape inclined from the outside to the through hole.

The sleep sensing unit 220 senses a sleeping state and a non-sleeping state using a sensor that is provided in the body frame.

The communication unit 230 communicates with the user terminal 120 in a wired or wireless manner.

The non-sleep alarm unit 240 outputs the alarm signal notifying that the sleeper wakes up from a sleeping state when he/she wakes up from the sleeping state to be in the non-sleeping state through the sleep sensing unit 220.

The sound output unit 250 outputs music or sound most suitable to enable a sleeper to get a sound sleep depending on the sound sleep control signal received from the user terminal 120.

The brainwave measurement unit 260 measures the brainwave of the sleeper to transmit the brainwave information to the user terminal 120. That is, the brainwave measurement unit 260 detects a current on a scalp using a sensing sensor configured of an electrode to measure an electrical signal of a brain including a delta wave, a theta wave, an alpha wave, a beta wave, and a gamma wave and transmits the measured electrical signal of the brain to the user terminal 120.

In this case, the delta wave is a brainwave that is observed when a sleeper is in a sound sleep and the theta wave is a brainwave generated at the time of concentrating mind to use information in a brain or concentrating a solution to a logical thinking problem. Further, the alpha wave is a brainwave generated at the time of concentrating mind to use information in a brain, the beta wave is a brainwave mainly generated at the time of doing physical activity or when a person is into something, and the gamma wave is a brainwave generated at the time of doing a high level of complex mind function.

Figure 3:
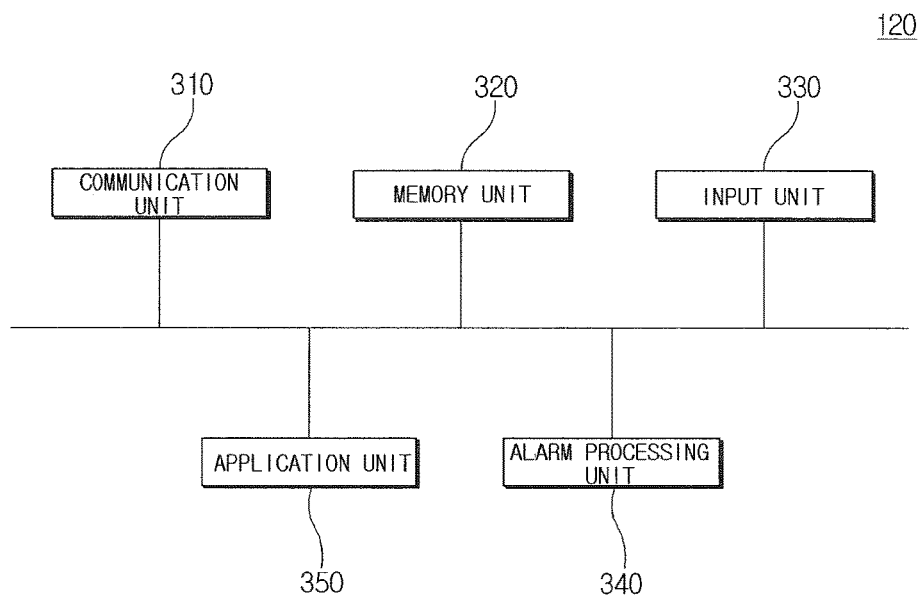
FIG. 3 is a diagram schematically illustrating an internal configuration of a user terminal according to an exemplary embodiment of the present invention.

FIG. 3 is a diagram schematically illustrating an internal configuration of a user terminal according to an exemplary embodiment of the present invention.

Referring to FIG. 3, the user terminal 120 according to the exemplary embodiment of the present invention includes a communication unit 310, a memory unit 320, an input unit 330, an alarm processing unit 340, and an application unit 350.

Here, the user terminal 120 includes a notebook computer, a desk top computer, or the like that may perform wireless communication or wired communication, including a smart phone or a PDA that may be carried by a user.

The user terminal 120 may have a structure in which an application that sets music, sound, or the like most suitable to enable a sleeper to get a sound sleep based on the brainwave information and then transmits the sound sleep control signal to the pillow 110 is installed in the application unit 350 of the terminal, or separate application programs may be installed in the terminal when the user terminal 120 is the notebook computer or the desk top computer.

The communication unit 310 communicates with the pillow 110 in a wired or wireless manner.

The memory unit 320 stores brainwave information and environment information including music or sound corresponding to the brainwave information.

The input unit 330 is used to selectively input either music or sound corresponding to the brainwave information.

The alarm processing unit 340 outputs the alarm signal received from the pillow on a screen or outputs the alarm signal as a sound.

The application unit 350 is controlled to transmit the sound sleep control signal that enables a sleeper to get a sound sleep based on the brainwave information of the sleeper, to the pillow 110.

Figure 4:
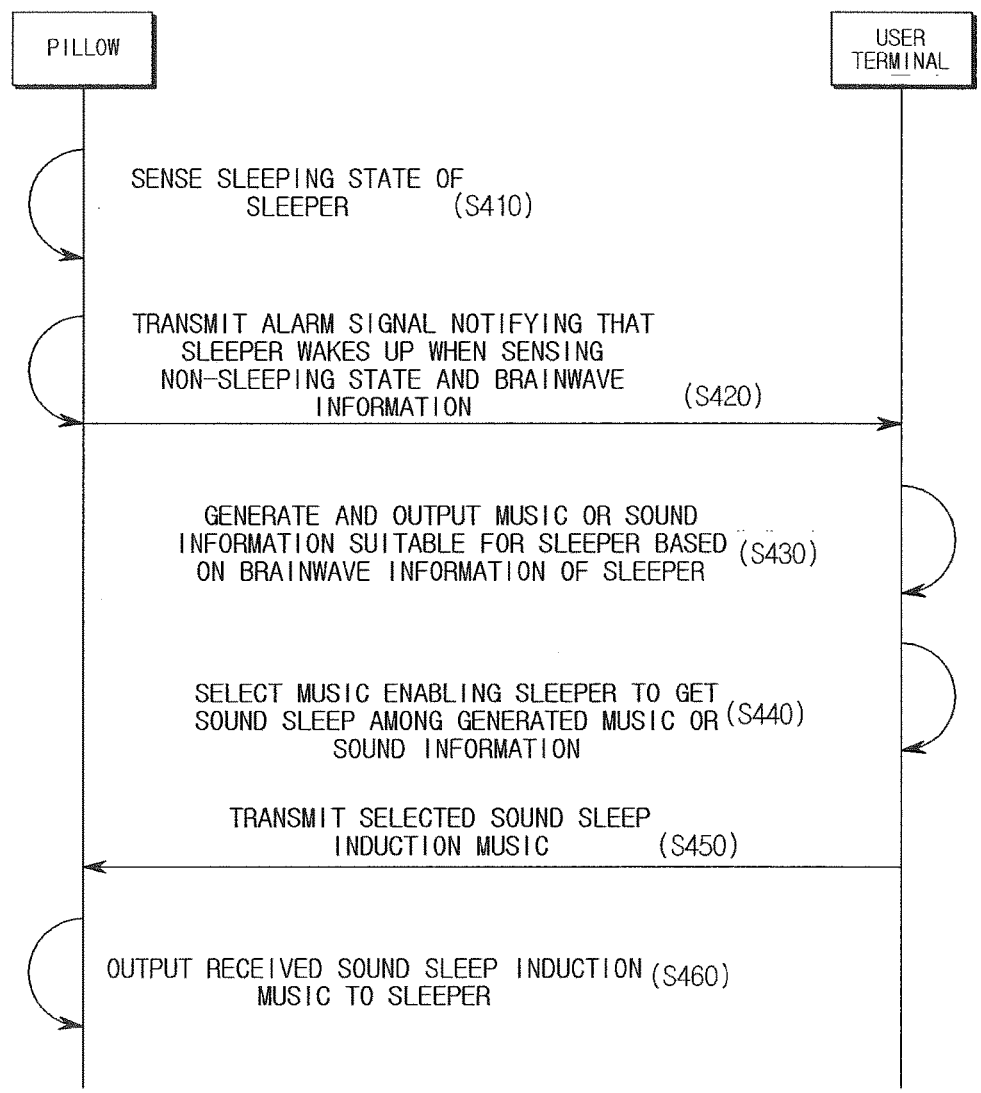
FIG. 4 is an operation flow chart for describing a method for controlling a sound sleep induction operation of a smart pillow system according to an exemplary embodiment of the present invention.

FIG. 4 is an operation flow chart for describing a method for controlling a sound sleep induction operation of a smart pillow system according to an exemplary embodiment of the present invention.

Referring to FIG. 4, in the smart pillow system 100 according to an exemplary embodiment of the present invention, first, the pillow 110 senses a sleeping state of a sleeper.

In this case, the pillow 110 may sense a change in pressure value pressed by a sleeper's head by a pressure sensor to sense a sleeping state of the sleeper.

Further, the pillow 110 may sense an operation state depending on tossing and turning of a sleeper after the sleeper wakes up from a sound sleep state by a motion sensing sensor.

Further, the pillow 100 may recognize that the sleeper is in the sound sleep state if the delta wave is sensed based on the brainwave information measured by the brainwave measurement unit 260 and recognize that the sleeper is in the non-sleeping state if the alpha wave, the beta wave, the gamma wave, or the like including the theta wave are sensed.

Next, when sensing the non-sleeping state, the pillow 110 transmits the alarm signal notifying that a sleeper wakes up from a sleeping state and the brainwave information to the user terminal 120 (S420).

In this case, the pillow 110 may receive crying or sound of a sleeper generated when the sleeper wakes up from the sound sleep state through a microphone to sense the non-sleeping state.

Next, the user terminal 120 generates and outputs music or sound information suitable for a sleeper based on the brainwave information of the sleeper.

Figure 5:
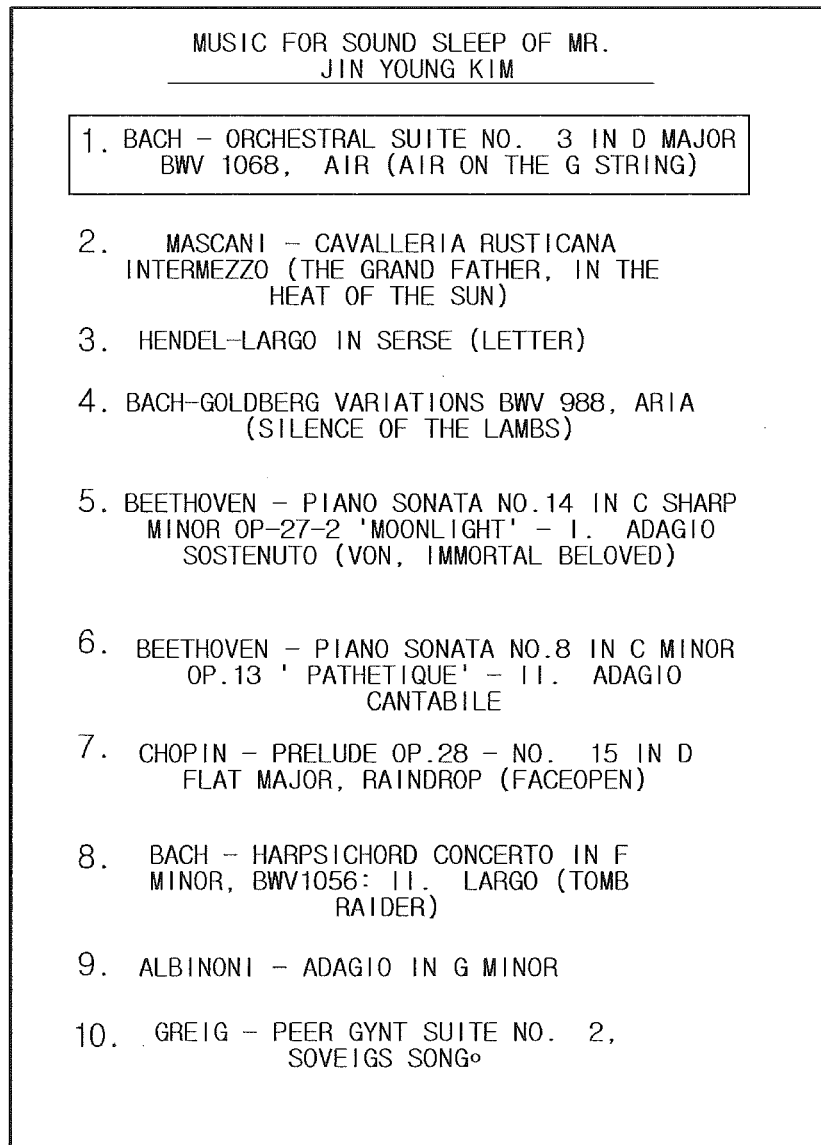
FIG. 5 is a diagram illustrating an example of selecting music corresponding to brainwave information of a current sleeper among sound and music corresponding to the brainwave information according to an exemplary embodiment of the present invention.

That is, as illustrated in FIG. 5, the user terminal 120 outputs the sound or music information corresponding to the current brainwave information of the sleeper on the screen among the sound or music information corresponding to the brainwave information stored in the memory unit 320. FIG. 5 is a diagram illustrating an example of selecting music corresponding to brainwave information of a current sleeper among sound and music corresponding to the brainwave information according to an exemplary embodiment of the present invention. For example, when a sleeper is in a sound sleep and thus the delta wave is sensed, a list of very quiet music corresponding to the delta wave to enable the sleeper to keep the sound state, music that helps the sleeper to keep a sound sleep, or the like is output.

Next, the user terminal 120 selects music enabling a sleeper to get a sound sleep depending on a user selection among sound or music output on the screen (S440).

That is, as illustrated in FIG. 5, the user terminal 120 outputs sound or music corresponding to the delta wave helping the sleeper to get the sound sleep when the sleeper wakes up from the sound sleep and thus the brainwave information of the sleeper is the beta wave and sets the music depending on the user selection among the output list as sound sleep induction music.

Next, the user terminal 120 transmits the selected sound sleep induction music to the pillow 110 (S450).

Therefore, the pillow 110 outputs the sound sleep induction music received from the user terminal 120 to the sleeper (S460).

That is, the pillow 110 outputs, for example, the music "Bach-Orchestral Suite No. 3 IN D major BMV 1068. AIR (Air on the G string)" selected as a sound sleep induction music as an audible sound through the sound output unit 250. Here, the sound output unit 250 includes a bone conduction speaker, or the like in addition to a micro speaker.

Therefore, music that enables a sleeper to automatically get a sound sleep when the sleeper wakes up while sleeping on the pillow 110 is provided through the speaker, such that the sleeper may directly get a sound sleep.

Figure 16:
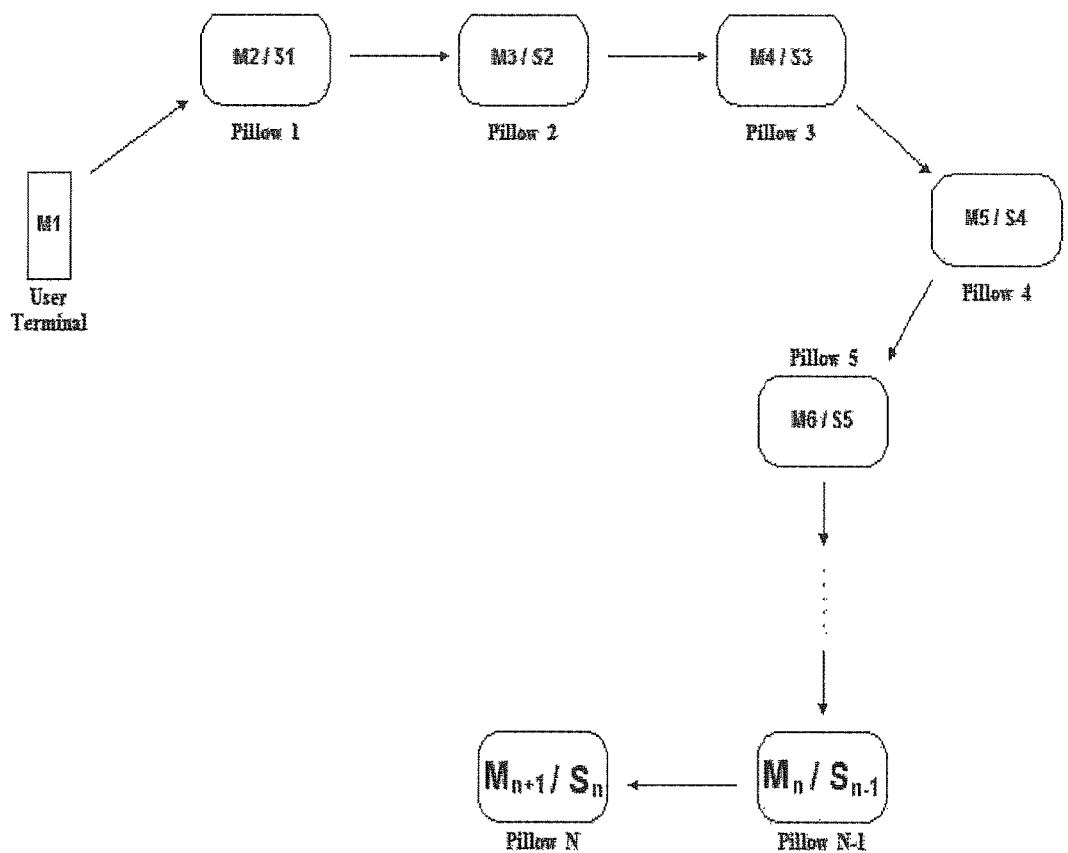
FIG. 16 is a diagram illustrating a process of transmitting a sound sleep control signal from a user terminal to a plurality of pillows when more than one pillow is present around the user terminal, according to an exemplary embodiment of the present invention.

Meanwhile, as illustrated in FIG. 16, more than one pillow 110 may be present around the user terminal 120. In this case, the user terminal 120 is operated as a first master terminal M1 and a first pillow M2/S1 at a shortest distance from the user terminal 120 is operated as a first slave terminal to transmit the sound sleep control signal from the user terminal 120 that is the first master terminal M1 to a first pillow Pillow 1 that is the first slave terminal S1 and the first pillow Pillow 1 is operated as a second master terminal M2 when a second pillow Pillow 2 is present at the shortest distance therefrom and the second pillow Pillow 2 is operated as a second slave terminal S2 to transmit the sound sleep control signal from the first pillow Pillow 1 that is the second master terminal M2 to the second pillow Pillow 2 that is the second slave terminal, and thus the pillows adjacent to each other at a short distance are operated as the master terminal and the slave terminal to operate an N−1-th pillow Pillow N−1 as an N-th master terminal Mn when an N-th pillow Pillow N is present at the shortest distance therefrom and operate the N-th pillow Pillow N as an N-th slave terminal Sn to thereby transmit the sound sleep control signal from the N−1-th pillow Pillow N−1 that is the N-th master terminal Mn to the N-th pillow Pillow N that is the N-th slave terminal Sn, such that as the sound sleep control signal is sequentially transmitted through a linear network from the first pillow Pillow 1 to the N-th pillow Pillow N, the first pillow Pillow 1 to the N-th pillow Pillow N are operated based on the sound sleep control signal In this case, when time taken to transmit the sound sleep control signal from one master terminal M to the slave terminal S is A seconds, time taken to transmit the sound sleep control signal from the user terminal 120 to the N-th pillow Pillow N through the first pillow Pillow 1 may be calculated as A seconds*N. For example, time taken to transmit the sound sleep control signal from one master terminal M to one slave terminal S is 0.3 seconds and when 10 pillows are present around the user terminal 120, time taken to transmit the sound sleep control signal from user terminal 120 to a tenth pillow Pillow 10 through the first pillow Pillow 1 is calculated as 0.3 seconds*10 and thus becomes 3 seconds.

Figure 6:
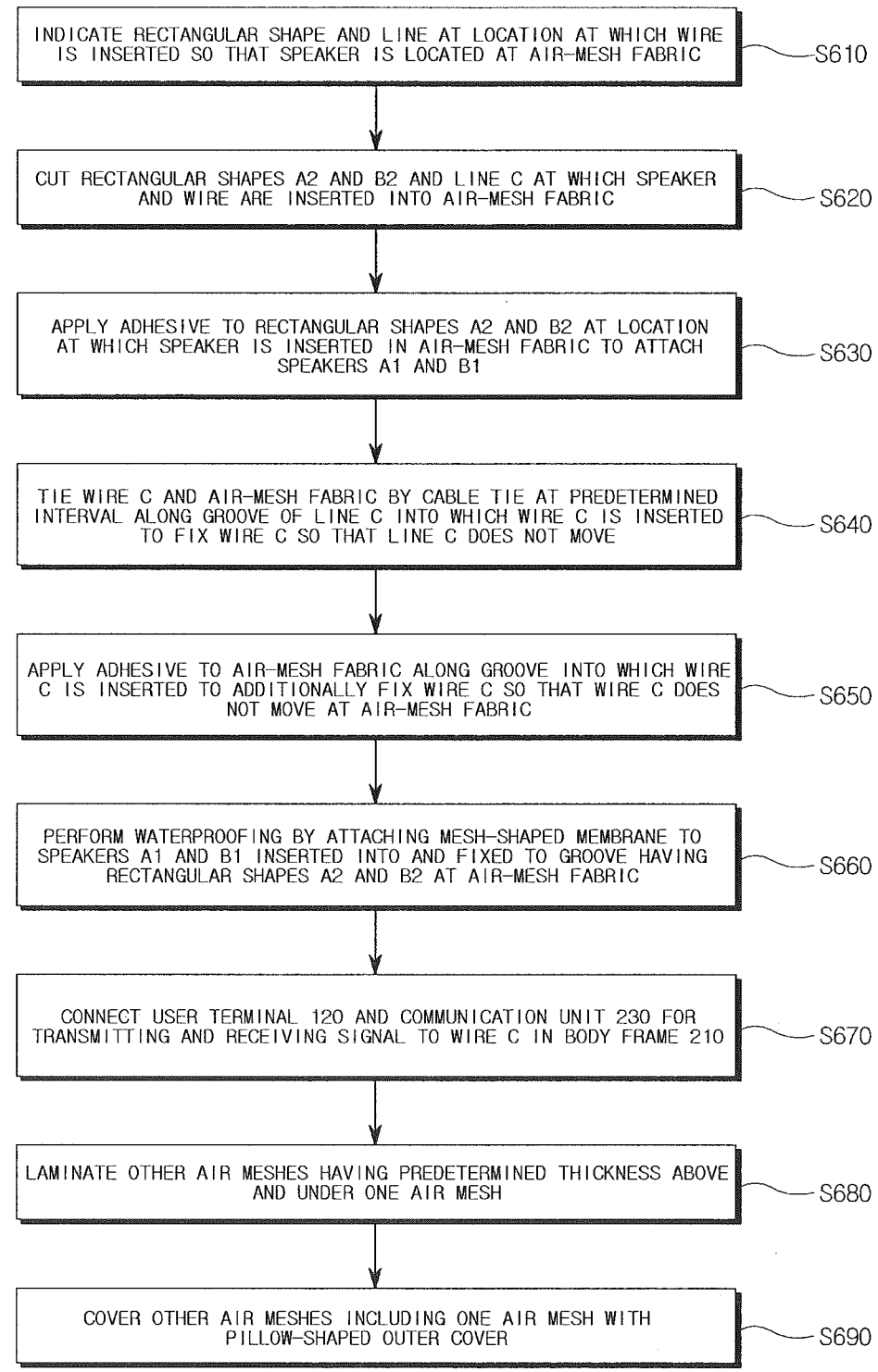
FIG. 6 is an operational flowchart for describing a method for manufacturing a smart pillow system according to an exemplary embodiment of the present invention.

FIG. 6 is an operational flowchart for describing a method for manufacturing a smart pillow system according to an exemplary embodiment of the present invention.

Figure 7:
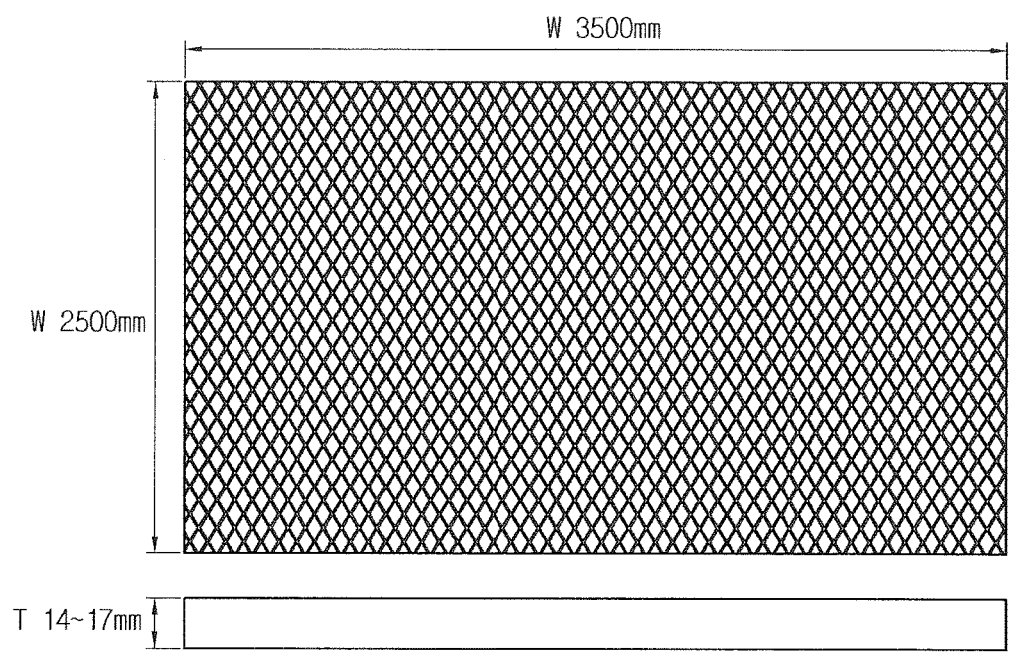
FIG. 7 is a diagram illustrating a double-sided air mesh for manufacturing a main body frame of a pillow according to an exemplary embodiment of the present invention.

Referring to FIG. 6, in the smart pillow system according to the exemplary embodiment of the present invention, a double-sided air-mesh having a predetermined thickness as illustrated in FIG. 7 is prepared as a diamond shape upon the manufacturing of the main body frame 210. FIG. 7 is a diagram illustrating a double-sided air mesh for manufacturing a main body frame of a pillow according to an exemplary embodiment of the present invention. As illustrated in FIG. 7, the double-sided air-mesh having 3500 mm in breadth, 2500 mm in length, and 14 to 17 mm in thickness is prepared.

Figure 8:
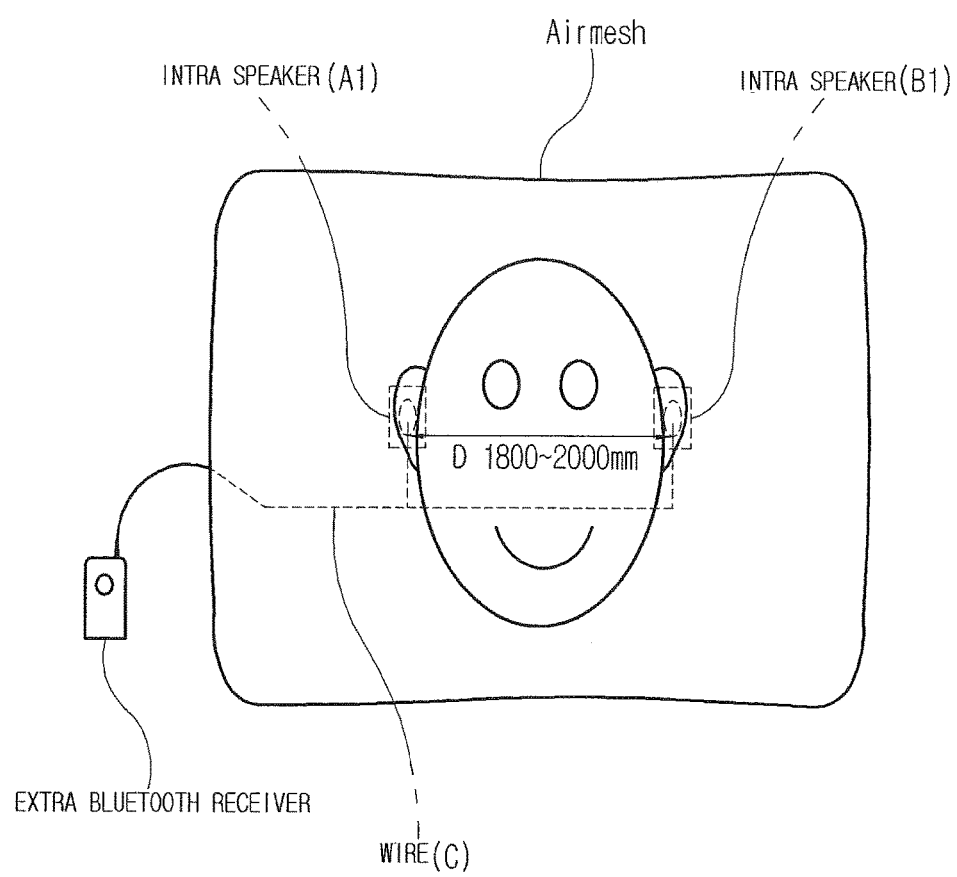
FIG. 8 is a diagram illustrating an example of a rectangular shape and a line indicated at a location at which a wire is inserted so that a speaker is located at an air-mesh fabric of a pillow, according to an exemplary embodiment of the present invention.

Next, as illustrated in FIG. 8, rectangular shapes A2 and B2 are indicated at the double-sided air-mesh fabric having a predetermined thickness in the may body frame 210 so that speakers A1 and B1 are located at points at which sleeper's ears are located when a sleeper's head is seated on a pillow, and a line C is indicated at a location at which the wire C is inserted (S610). FIG. 8 is a diagram illustrating an example of a rectangular shape and a line indicated at a location at which a wire is inserted so that a speaker is located at an air-mesh fabric of a pillow, according to an exemplary embodiment of the present invention. As illustrated in FIG. 8, the speakers A1 and B1 are indicated at the double-sided air-mesh fabric and rectangular shapes A2 and B2 and the line C are indicated at the location at which the wire C is inserted. In this case, a distance D between location A2 and location B2 at which the speakers are seated ranges from 1800 mm to 2000 mm. The reason is that a standard horizontal distance between a right ear tragus a1 and a left ear tragus b2 of a general adult ranges from 1800 mm to 2000 mm. Therefore, as the speakers approach locations of both ears, a sound in a stereo scheme may be more effectively transferred to a person who is lying with his/her head on a pillow.

Figure 9:
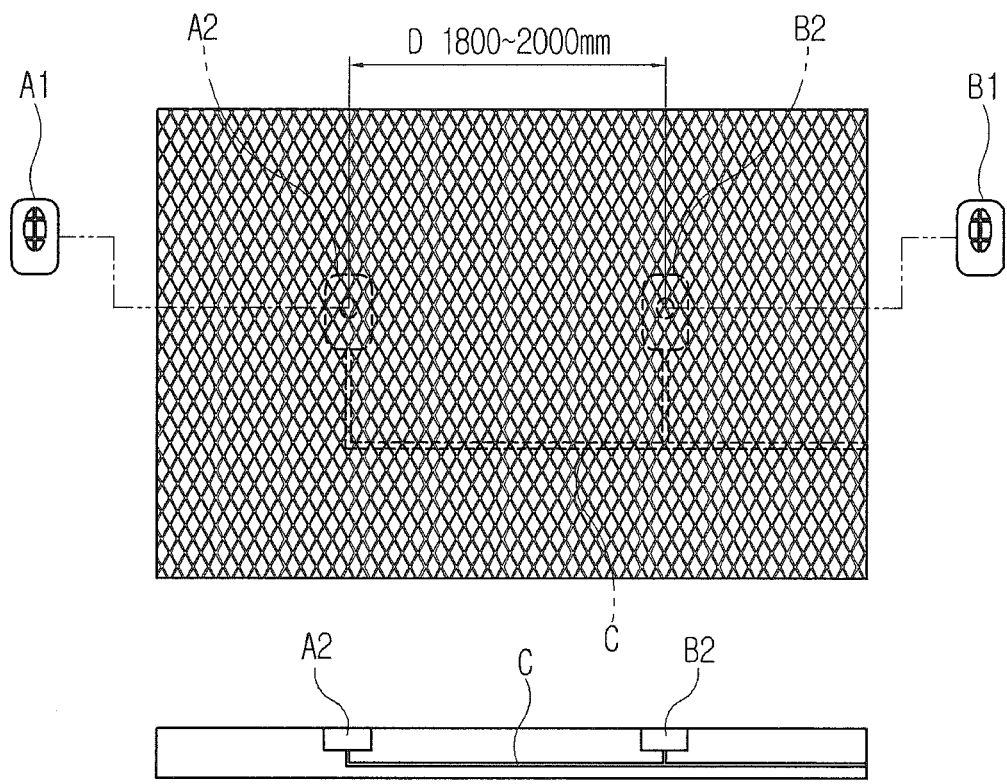
FIG. 9 is a diagram illustrating an example of cutting the air-mesh fabric to insert the speaker and the wire, according to the exemplary embodiment of the present invention.

Next, at the double-sided air-mesh fabric in the main body frame 210, as illustrated in FIG. 9, the rectangular shapes A2 and B2 into which the speakers A1 and B1 and the wire C are inserted and the line C are cut (S620). FIG. 9 is a diagram illustrating an example of cuffing the air-mesh fabric to insert the speaker and the wire, according to the exemplary embodiment of the present invention. That is, in the case of the main body frame 210, as illustrated in FIG. 9, at the double-sided air-mesh fabric, the rectangular shapes A2 and B2 and the wire C at the locations at which the speakers A1 and B1 and the wire C are inserted are cut along the shapes of the speakers A2 and B2 and the shape of the line C. In this case, like F1, it is not completely cut but is cut only by half. That is, it is cut by a scheme of digging a groove as much as a half of a thickness of the air-mesh fabric.

Figure 10:
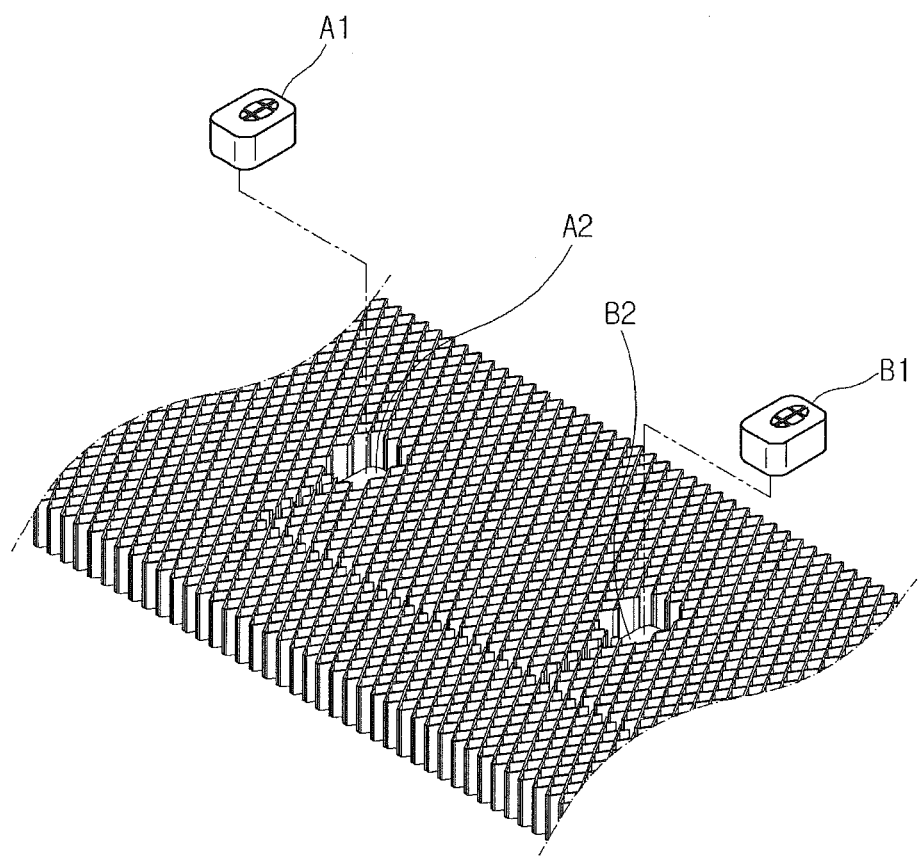
FIG. 10 is a diagram illustrating an example in which a rectangular groove and a long groove along a line shape in which the wire is inserted are formed at a location at which the speaker is inserted into the air-mesh fabric, according to an exemplary embodiment of the present invention.

Therefore, as illustrated in FIG. 10, a long groove is formed in a line shape along the line C into which the wire C is inserted and a shape in which the groove is dug at the locations at which the speakers A1 and B1 are inserted in the rectangular shapes A2 and B2 is achieved. FIG. 10 is a diagram illustrating an example in which a rectangular groove and a long groove along a line shape in which the wire is inserted are formed at a location at which the speaker is inserted into the air-mesh fabric, according to an exemplary embodiment of the present invention.

Figure 11:
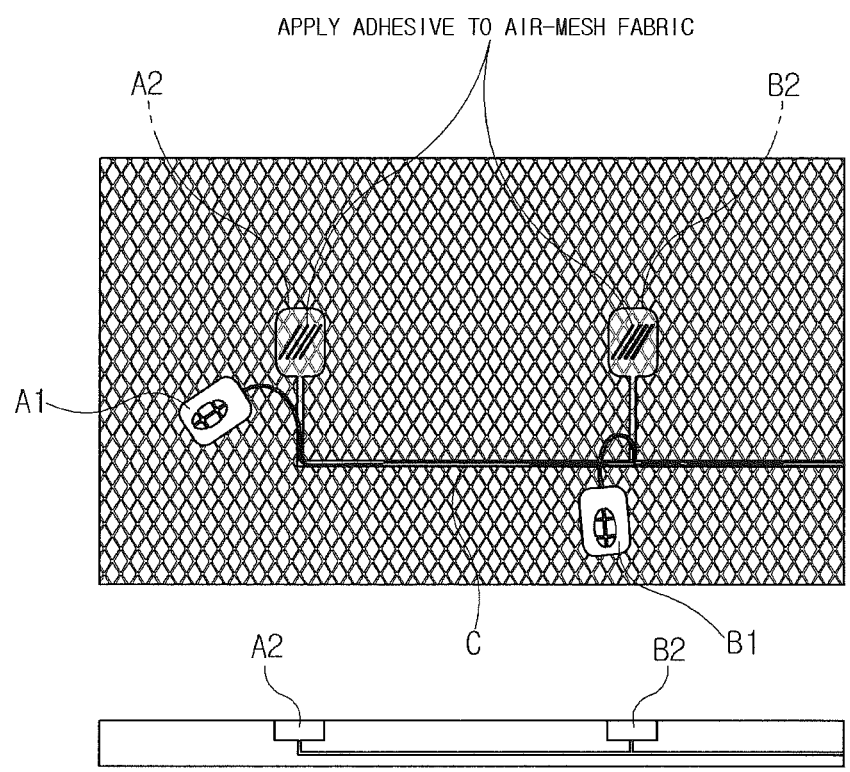
FIG. 11 is a diagram illustrating an example of attaching the speaker to the rectangular shape of the location at which the speaker is inserted into the air-mesh fabric, according to an exemplary embodiment of the present invention.

Next, at the rectangular shapes A2 and B2 at the air-mesh fabric in the main body frame 210, as illustrated in FIG. 11, an adhesive is applied to the rectangular shapes A2 and B2 at the locations into which the speakers A1 and B1 are inserted and the speakers A1 and B1 are attached (S630) FIG. 11 is a diagram illustrating an example of attaching the speaker to the rectangular shape of the location at which the speaker is inserted into the air-mesh fabric, according to an exemplary embodiment of the present invention. As illustrated in FIG. 11, the wire C is inserted along the groove of the line C previously cut on the air mesh.

Figure 12:
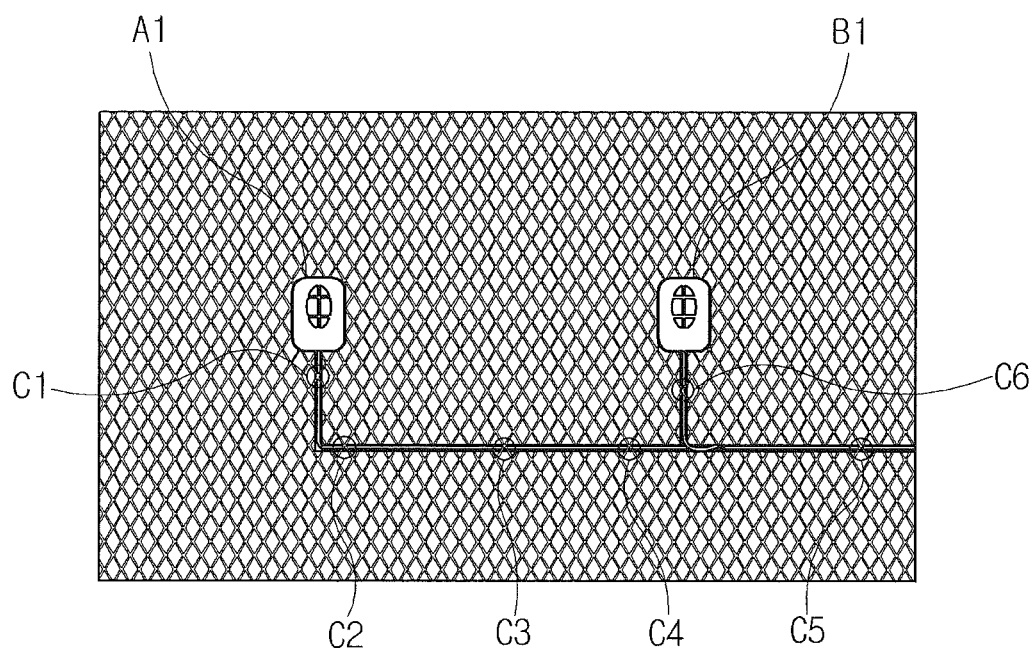
FIG. 12 is a diagram illustrating an example of tying and fixing the wire and the fabric by a cable tie at a predetermined interval along the groove into which the wire is inserted, according to an exemplary embodiment of the present invention.

Next, at the air-mesh fabric in the main body frame 210, as illustrated in FIG. 12, the wire C and the air-mesh fabric are tied at locations C1, C2, C3, C4, C5, and C6 by the cable tie at a predetermined interval along the groove of the line C into which the wire C is inserted to fix the line C so that the line does not move. FIG. 12 is a diagram illustrating an example of tying and fixing the wire and the fabric by a cable tie at a predetermined interval along the groove into which the wire is inserted, according to an exemplary embodiment of the present invention. Therefore, the line C connected to the speakers A1 and B1 may maintain the fixed state not to move despite the twist or fluctuation of the pillow due to the motion of the sleeper.

Figure 13:
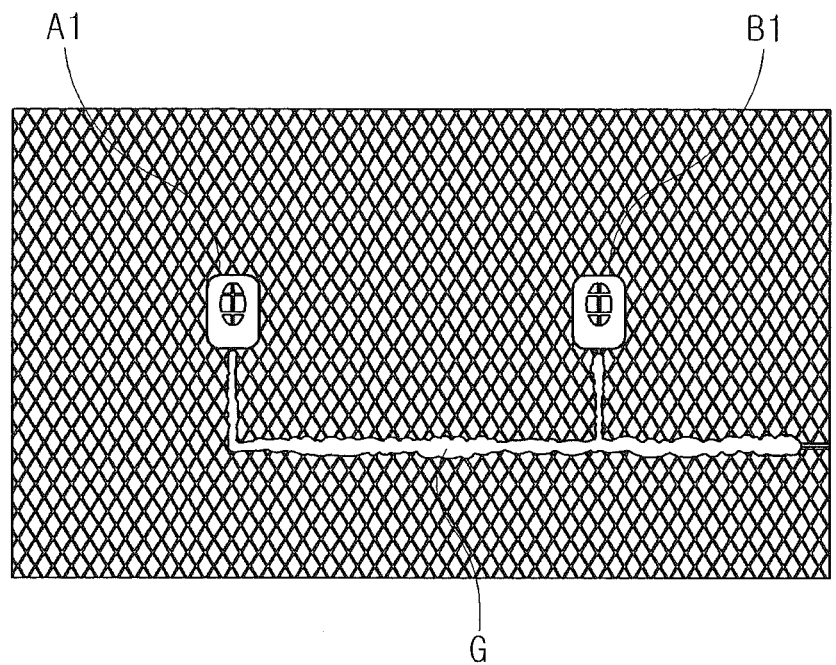
FIG. 13 is a diagram illustrating an example of applying an adhesive to the air-mesh fabric along the groove into which the wire is inserted and additionally fixing the wire to prevent the wire from moving at the air-mesh fabric, according to an exemplary embodiment of the present invention.

Next, at the air-mesh fabric in the main body frame 210, as illustrated in FIG. 13, the adhesive (for example, glue gun) is applied along the groove into which the wire C is inserted and thus the wire C is additionally fixed not to move at the air-mesh fabric (S650). FIG. 13 is a diagram illustrating an example of applying an adhesive to the air-mesh fabric along the groove into which the wire is inserted and additionally fixing the wire to prevent the wire from moving at the air-mesh fabric, according to an exemplary embodiment of the present invention. In this case, when an adhesive G such as glue gun is applied along the line-shaped groove in which the wire C is inserted, the line-shaped groove and the wire C both are applied with the adhesive G by a method for filling a line-shaped groove. Therefore, the line C connected to the speakers A1 and B1 is applied with the adhesive even though the pillow moves, and thus is in a state in which the line C is bonded to the air-mesh fabric not to move.

Figure 14:
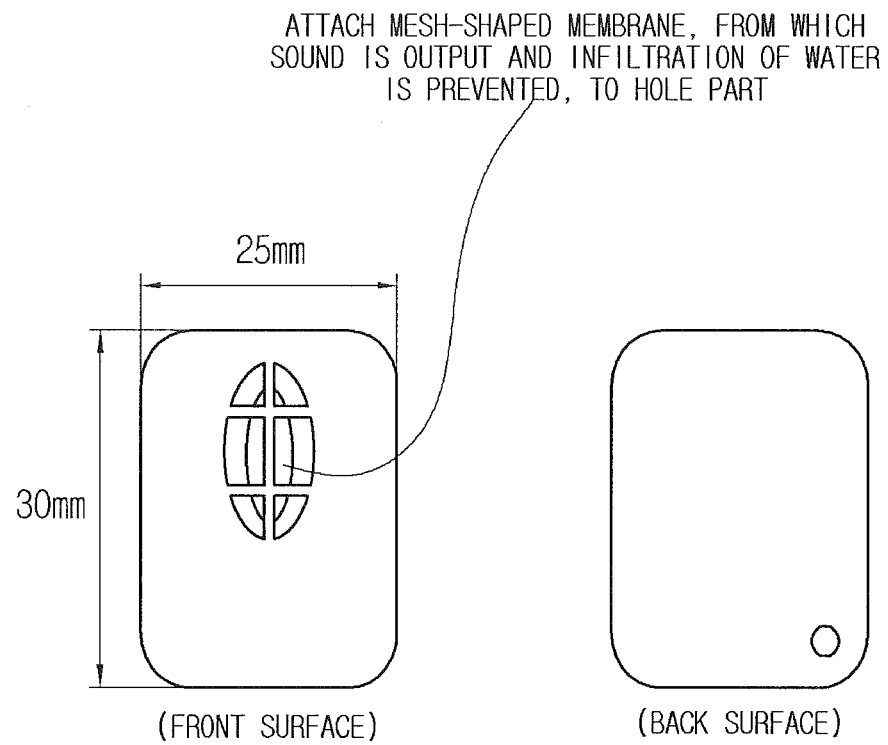
FIG. 14 is a diagram illustrating an example of attaching and waterproofing a mesh-shaped membrane to the speaker inserted into the rectangular groove of the air-mesh fabric, according to an exemplary embodiment of the present invention.

Next, at the air-mesh fabric in the main body frame 210, as illustrated in FIG. 14, the speakers A1 and B1 that are inserted into and fixed to the grooves having the rectangular shapes A2 and B2 are waterproofed while being attached with the mesh-shaped membrane. FIG. 14 is a diagram illustrating an example of attaching and waterproofing a mesh-shaped membrane to the speaker inserted into the rectangular groove of the air-mesh fabric, according to an exemplary embodiment of the present invention. As illustrated in FIG. 14, the speakers A1 and B1 fixed to the air-mesh fabric are finally sealed while being attached with the mesh-shaped membrane, and therefore sound comes out from a circumference of a hole to which the speakers A1 and B1 are fixed and water is prevented from being infiltrated into the circumference of the hole, thereby obtaining the waterproofing effect. Here, the speakers A1 and B1 may be fixed in a size of 25 mm in breadth and 30 mm in length.

Figure 15:
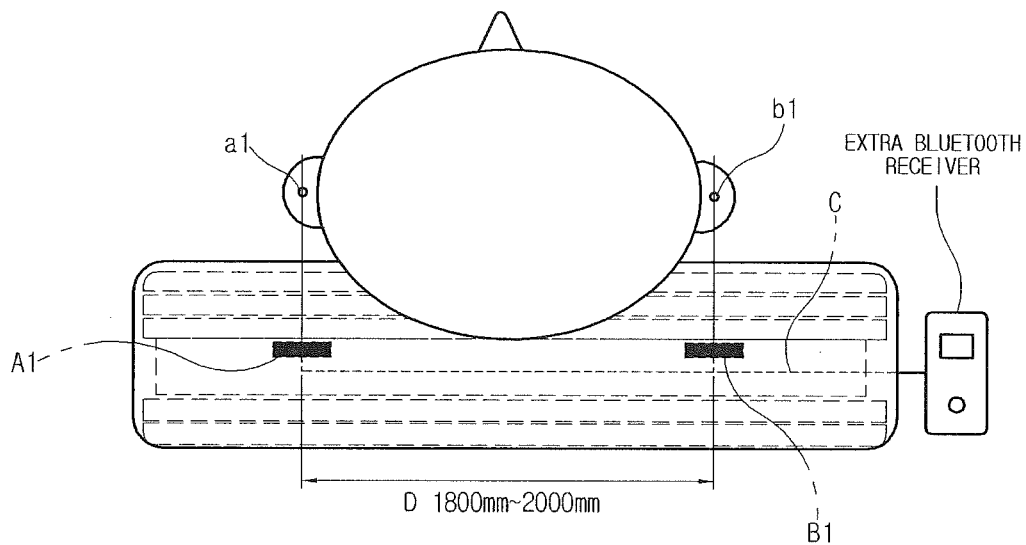
FIG. 15 is a diagram illustrating an example in which the speaker in the pillow is fixed at a location corresponding to an ear tragus part to transfer sound sleep induction music from the speaker well, according to an exemplary embodiment of the present invention.
Figure 15:
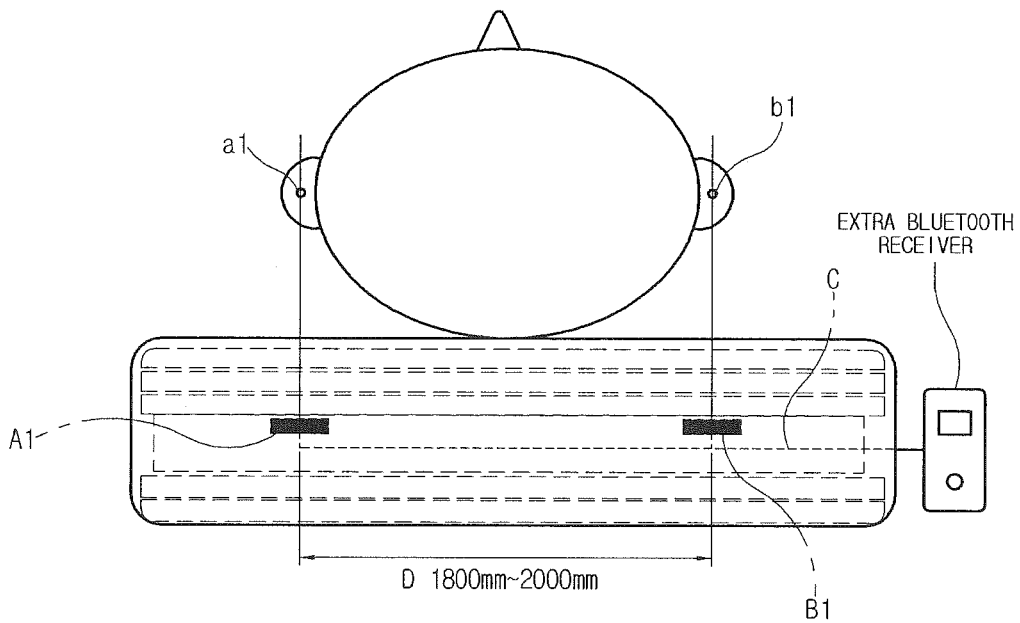

Therefore, when a sleeper seats on the pillow 110 and gets sleep, as illustrated in FIG. 15, the left ear tragus part a1 and the right ear tragus part b1 of the sleeper are located to correspond to the locations at which the speakers A1 and B1 are located in the air-mesh fabric, such that music output from the speakers A1 and B1 is transferred to the ear of the sleeper well. FIG. 15 is a diagram illustrating an example in which the speaker in the pillow is fixed at a location corresponding to an ear tragus part to transfer sound sleep induction music from the speaker well, according to an exemplary embodiment of the present invention. As illustrated in FIG. 15, a distance between the left speaker A1 and the right speaker B1 range approximately from 1800 mm to 2000 mm, like the distance between the left ear tragus a1 and the right ear tragus b1 of a general adult sleeper.

Next, the wire c in the body frame 210 is connected to the communication unit 230 for transmitting and receiving a signal to and from the user terminal 120 (S670).

Therefore, the communication unit 230 is connected to the speakers A1 and B1 in the pillow 110 by the wire C and the communication unit 230 may be implemented as, for example, an extra Bluetooth receiver, or the like.

Next, as illustrated in FIG. 15, other air meshes having a predetermined thickness are laminated above and under one air mesh (S680).

Further, other laminated air meshes including one air mesh is covered with a pillow-shaped cover (S690).

That is, the air meshes having a thickness of 14 to 17 mm illustrated in FIG. 7 are laminated in the cover of the pillow 110 to form the pillow shape.

As described above, the present invention is to provide the smart pillow system and the method for manufacturing the same capable of notifying the user's smart phone managing the sleeper of the case in which the sleeper wakes up while the sound sleep state of the sleeper who is sleeping on the pillow is sensed and providing the music or the sound most suitable to enable the sleeper to get a sound sleep based on the brainwave information of the sleeper to the sleeper through the pillow, to thereby enable the sleeper to get the sound sleep again.

Those skilled in the art will appreciate that since various modifications and alterations may be made without departing from the spirit or essential feature of the present invention, the above-mentioned embodiments are not restrictive but are exemplary in all aspects. It should be interpreted that the scope of the present invention is defined by the following claims rather than the above-mentioned detailed description and all modifications or alterations deduced from the meaning, the scope, and equivalences of the claims are included in the scope of the present invention.

INDUSTRIAL APPLICABILITY

The present invention may be applied to the smart pillow system and the method for manufacturing the same capable of notifying the user's smart phone managing the sleeper of the case in which the sleeper wakes up while the sound sleep state of the sleeper who is sleeping on the pillow is sensed and providing the music or the sound most suitable to enable the sleeper to get a sound sleep based on the brainwave information of the sleeper to the sleeper through the pillow, to thereby enable the sleeper to get the sound sleep again.

The invention claimed is:

1. A smart pillow system including a pillow, wherein one air mesh is provided with a speaker-shaped groove and a line-shaped groove by cutting each of locations at which a speaker and a wire are inserted, the speaker is attached to the speaker-shaped groove by an adhesive, the wire is inserted into the line-shaped groove and is tied by a cable tie to be fixed, the adhesive is applied along the line-shaped groove into which the wire is inserted, the speaker is attached with a mesh-shaped membrane for waterproofing, a communication unit for transmitting and receiving a signal to and from a user terminal is connected to the wire, other air meshes are laminated above and under the one air mesh, and the other air meshes including the one air mesh are covered with a pillow-shaped outer cover, wherein the pillow generates an alarm signal when sensing that a sleeper wakes up from a sleeping state and is thus in a non-sleeping state, measures a brainwave of the sleeper and transmits a measured brainwave information of the sleeper to the user terminal through the communication unit along with the alarm signal, and receives a sound sleep control signal based on the brainwave information of the sleeper from the user terminal to output a music or a sound to enable the sleeper to get a sound sleep in which the brainwave of the sleeper is a delta wave, and the user terminal receives from the pillow the brainwave information of the sleeper along with the alarm signal notifying that the sleeper wakes up from the sleeping state and transmits the sound sleep control signal including the music or the sound suitable to enable the sleeper to keep the sound sleep based on the brainwave information of the sleeper to the pillow, and wherein when more than one pillow is present around the user terminal, the user terminal is operated as a first master terminal and a first pillow at a shortest distance from the user terminal is operated as a first slave terminal to transmit the sound sleep control signal from the user terminal that is the first master terminal to the first pillow that is the first slave terminal and the first pillow is operated as a second master terminal when a second pillow is present at the shortest distance therefrom and the second pillow is operated as a second slave terminal to transmit the sound sleep control signal from the first pillow that is the second master terminal to the second pillow that is the second slave terminal, and thus the pillows adjacent to each other at a short distance are operated as the master terminal and the slave terminal to operate an N−1-th pillow as an N-th master terminal when an N-th pillow is present at the shortest distance therefrom and operate the N-th pillow as an N-th slave terminal to thereby transmit the sound sleep control signal from the N−1-th pillow that is the N-th master terminal to the N-th pillow that is the N-th slave terminal, such that as the sound sleep control signal is sequentially transmitted through a linear network from the first pillow to the N-th pillow, the first pillow to the N-th pillow are operated based on the sound sleep control signal.

2. The smart pillow system of claim 1, wherein the pillow communicates with the user terminal through the communication unit in a wired or wireless manner and includes:

a main body frame configured to support a head of the sleeper;

a sleep sensing unit configured to determine a sleeping state and a non-sleeping state using a sensing sensor included in the main body frame;

a brainwave measurement unit configured to measure the brainwave of the sleeper and transmit the measured brainwave information to the user terminal;

a non-sleep alarm unit configured to output an alarm signal notifying that the sleeper wakes up from the sleeping state when the non-sleeping state of the sleeper is sensed by the sleep sensing unit; and a sound output unit configured to output the music or the sound that enables the sleeper get the sound sleep depending on a sound sleep control signal received from the user terminal.

3. The smart pillow system of claim 1, wherein when time taken to transmit the sound sleep control signal from the master terminal to the slave terminal is A seconds, time taken to transmit the sound sleep control signal from the user terminal to the N-th pillow through the first pillow is calculated as A seconds*N.

4. The smart pillow system of claim 1, wherein the user terminal includes:

a memory unit configured to store environment information including the music or the sound corresponding to the brainwave information;

an input unit configured to select the music or the sound corresponding to the brainwave information;

an alarm processing unit configured to output the alarm signal received from the pillow on a screen or output the alarm signal as a sound; and an application unit configured to transmit the sound sleep control signal, that enables the sleeper to get the sound sleep based on the brainwave information of the sleeper, to the pillow.

5. The smart pillow system of claim 3, wherein the main body frame has a central part provided with a through hole so that a head of the sleeper is seated and has a pillow shape in which an air mesh having a concave shape inclined from an outside to the through hole is laminated sheet by sheet, and has a concave shape inclined from the outside to the through hole.

6. The smart pillow system of claim 3, wherein the brainwave measurement unit detects a current on a scalp using a sensing sensor configured of an electrode to measure an electrical signal of a brain including the delta wave, a theta wave, an alpha wave, a beta wave, and a gamma wave.

* * * * *